(12) United States Patent
Muhlsteff et al.

(10) Patent No.: US 8,548,577 B2
(45) Date of Patent: Oct. 1, 2013

(54) DETECTION OF ELECTRICAL AND MECHANICAL CARDIO-VASCULAR ACTIVITIES

(75) Inventors: Jens Muhlsteff, Aachen (DE); Jeroen Adrianus Johannes Thijs, Waldfeucht (DE); Robert Pinter, Aachen (DE)

(73) Assignee: Koninklijke Philips N.V., Eindhoven (NL)

(*) Notice: Subject to any disclaimer, the term of this patent is extended or adjusted under 35 U.S.C. 154(b) by 624 days.

(21) Appl. No.: 12/680,943

(22) PCT Filed: Oct. 2, 2007

(86) PCT No.: PCT/IB2007/054004
§ 371 (c)(1),
(2), (4) Date: Mar. 31, 2010

(87) PCT Pub. No.: WO2009/044230
PCT Pub. Date: Apr. 9, 2009

(65) Prior Publication Data
US 2010/0217118 A1    Aug. 26, 2010

(51) Int. Cl.
*A61B 5/04* (2006.01)

(52) U.S. Cl.
USPC .......... 600/513; 600/407; 600/430; 600/481; 600/508; 600/509; 600/522; 600/523

(58) Field of Classification Search
USPC ............... 600/407, 430, 481, 508, 509, 513, 600/522, 523
See application file for complete search history.

(56) References Cited

U.S. PATENT DOCUMENTS

| | | | |
|---|---|---|---|
| 5,012,411 A * | 4/1991 | Policastro et al. | 600/485 |
| 5,113,869 A * | 5/1992 | Nappholz et al. | 600/508 |
| 5,554,177 A | 9/1996 | Kieval et al. | |
| 6,126,595 A * | 10/2000 | Amano et al. | 600/300 |
| 6,496,715 B1 | 12/2002 | Lee et al. | |
| 6,694,178 B1 | 2/2004 | Soula et al. | |
| 7,174,203 B2 | 2/2007 | Arand et al. | |
| 2001/0056245 A1* | 12/2001 | Mlynash et al. | 600/513 |
| 2002/0120184 A1 | 8/2002 | Beck et al. | |
| 2005/0215947 A1 | 9/2005 | Heruth et al. | |
| 2006/0017558 A1* | 1/2006 | Albert et al. | 340/531 |
| 2006/0100535 A1 | 5/2006 | Bauer | |
| 2006/0106322 A1 | 5/2006 | Arand et al. | |

FOREIGN PATENT DOCUMENTS

WO    2007010460 A2    1/2007

OTHER PUBLICATIONS

"The use of a two channel Doppler radar sensor for the characterization of heart motion phases" by J. Muehlsteff et al. Proceedings of the 28th IEEE. New York City. Aug. 30-Sep. 3, 2006. pp. 547-550.*

(Continued)

*Primary Examiner* — Tse Chen
*Assistant Examiner* — Jason Ip

(57) ABSTRACT

A device detects electrical and mechanical cardio-vascular activities of patient, especially early decompensation detection of congestive heart failure patients (CHF). The device includes a transmitter for transmitting electromagnetic signals of a predefined frequency into the chest of the patient, a Doppler radar sensor (1) for detecting a Doppler radar signal reflected in the patient's chest, and an ECG unit (3) for capturing an ECG signal of the patient's heart. This device allows for simultaneous detection of electrical and mechanical cardio-vascular activities of a patient which can be used in an easy and reliable way and which allows for implementation in a hand-held or wearable device.

12 Claims, 3 Drawing Sheets

(56) References Cited

OTHER PUBLICATIONS

Muehlsteff et al: "A Handheld Device for Simultaneous Detection of Electrical and Mechanical Cardio-Vascular Activities With Synchronized ECG and CW-Doppler Radar"; Proceedings of the 29th Annual International Conference of the IEEE EMBS, Aug. 2007, pp. 5758-5761.

* cited by examiner

DETECTION OF ELECTRICAL AND MECHANICAL CARDIO-VASCULAR ACTIVITIES

FIELD OF THE INVENTION

The invention relates to the field of detection of electrical and mechanical cardio-vascular activities of a patient, especially to early decompensation detection of congestive heart failure patients (CHF).

BACKGROUND OF THE INVENTION

Congestive heart failure (CHF) is related to any structural or functional cardiac disorder that impairs the ability of the heart to fill with or pump a sufficient amount of blood throughout the body. CHF often remains undiagnosed and is associated with an annual mortality of 10%. Patients with heart failure cannot exert themselves because they become short of breath and tired. Often, swelling in the legs and ankles is observed. However, such swelling can be observed in other parts of the body, too. Sometimes, fluid collects in the lungs and interferes with breathing, causing shortness of breath, especially when the patient is lying.

The treatment of CHF focuses on treating the symptoms and signs of CHF and preventing the progression of the disease. Due to that, CHF patients have to perform daily measurements at home of weight, pulse, and blood pressure. Based on these measurements, the progression and health status of the specific patient is evaluated and the medication is adapted accordingly.

Accordingly, monitoring of CHF patients often requires activities at the patient's home which should be performed by the patient himself. Electrocardiogram (ECG) measurements have a long history in personal healthcare as a standard tool for observing the performance of a patient's electrical heart muscle excitation. On the market, small hand-held devices can be found which provide the patients with the possibility of easy ECG measurement at home.

However, the ECG signal, which is the electrical activation of the heart muscle, is not sufficient for an improved diagnosis. There is a clear need for measuring the mechanical actions of the heart. In order to meet this need, from US 2006/0106322 A1 it is known to monitor vital parameters related to CHF diagnosis based on a synchronised measurement of ECG signals and acoustical heart sounds. This technology uses well-known acoustical cardiography to access dyssynchrony of the heart chambers and to have access to additional hemodynamic parameters. However, this method is not suitable for home healthcare since the placement of the acoustical sensors is critical and cannot be done by the patient himself or any other untrained person.

SUMMARY OF THE INVENTION

It is an object of the invention to provide a device and a method for detection of electrical and mechanical cardio-vascular activities of a patient which can be used in an easy and reliable way and which allow for implementation in a hand-held or wearable device.

This object is achieved by a device for detection of electrical and mechanical cardio-vascular activities of a patient, comprising:

a transmitter for transmitting electromagnetic waves of a predefined frequency into the chest of the patient, a receiver for receiving reflected Doppler frequency shifted electromagnetic waves, and an ECG unit for capturing an ECG signal of the patient's heart.

Further, this object is also achieved by a method for cardiac decompensation detection, comprising the steps of transmitting electromagnetic signals of a predefined frequency into the chest of the patient, detecting a Doppler radar signal reflected in the patient's chest, and capturing an ECG signal of the patient's heart.

Accordingly, it is an important feature of the invention to combine ECG measurement with Doppler radar measurement in order to have the possibility of accessing not only electrical heart signals but also mechanical heart signals, which is of great importance for CHF diagnosis. Due to the use of Doppler radar measurements, the according device is easy to use, especially since no special positions on the chest for transmitting the electromagnetic wave like for ultrasound is required.

In general, the device for detection of electrical and mechanical cardio-vascular activities does not require any further measuring possibilities additional to the units for ECG and Doppler radar measurements, respectively. However, according to a preferred embodiment of the invention, the device further comprises an acceleration sensor for posture and/or activity detection of the patient. Such an acceleration sensor is advantages since erroneous measurements due to too much patient movement or due to wrong posture of the patient can be detected and avoided.

The device may comprise an internal data display and/or different types of plugs for data transfer. However, according to a preferred embodiment of the invention, the device comprises a wireless interface for wireless data communication with an external sender and/or receiver. This provides for the possibility of leaving the device in place, e. g. on a patient's body, even when data is transferred to some other unit for further analysis and/or processing. This wireless interface may allow for a bluetooth or W-LAN connection.

As already stated above, placement of the device for detection of electrical and mechanical cardio-vascular activities according to the invention is not critical for single measurements. Thus, in general, no measures for positioning aid are necessary. However, for repeated measurements it is preferred that the device is placed at the same position on the body for each consecutive measurement in order to ensure a reliable evaluation of the measured signals. Therefore, according to a preferred embodiment of the invention a positioning indicator for indicating a correct position of the device on the patient's chest and/or for indicating necessary movements of the device in order to achieve the correct position, based on an ECG signal and/or on an acceleration sensor signal, is provided.

Though, in general, ECG and Doppler radar signals can be received for many different placements of the device, there might be preferred placements leading to better S/N-ratios. This helps to improve the reliability of the measurements. Using multiple ECG electrodes, as it is proposed here, it is possible to measure different ECG vectors that can be used to position the device on the thorax. The best position is marked by typical ECG vectors that can then be used to guide the patient towards the right position. Similar to that, using the acceleration sensor, it is possible to track the position and/or angle of the device with respect to the earth gravity field. Accordingly, the patient can be guided to the correct position of the device.

Alternatively or additionally, according to a further preferred embodiment of the invention, the device further comprises a posture indicator for indicating a correct posture of the patient and/or for indicating necessary movements of the patient in order to achieve the correct posture, based on an ECG signal or on an acceleration sensor signal. This way, continuous measurement conditions, e.g. sitting, lying, or standing of the patient, can be maintained.

The measured ECG and Doppler radar signals can be used and processed in multiple ways. However, according to a preferred embodiment of the invention, the device further comprises a storage for successively storing at least one parameter of the Doppler radar signal and/or the ECG signal, a monitoring unit for monitoring and analyzing the stored parameters, and a warning unit for generating a warning signal if analysis of the stored parameters indicates a critical health situation of the patient. Accordingly, especially for decompensation detection, several different parameters from the Doppler radar signal and the ECG signal can be extracted, like pre-ejection period, time differences between Q or R peak and peak in the Doppler radar signal, heart contractility, cardiac output etc. If these parameters are stored and saved over a longer period these parameters can be analyzed, especially with respect to their trend, and, thus, the health situation of the patient can be monitored. In case the situation deteriorates, a warning signal can be generated, which means that the patient and/or medical staff is informed about the patient's condition and which further means that additional actions can be taken.

The device according to the invention comprises both the possibilities of detecting ECG and Doppler radar signals. Though it is not compulsory that the Doppler radar signal and the ECG signal are captured at the same time, according to a preferred embodiment of the method for cardiac decompensation detection, the Doppler radar signal and the ECG signal are captured simultaneously, at least for some duration. Capturing both kinds of signals simultaneously is advantageous since analysis benefits from multiple information due to different kinds of signals for the same sequence of heart contractions.

As already stated above, according to a preferred embodiment of the invention, for each of multiple Doppler signal and ECG signal measurements, at least one parameter of the Doppler radar signal and/or the ECG signal are stored. With respect to this, according to another preferred embodiment of the invention, at least one parameter of a first Doppler signal measurement and/or of a first ECG signal measurement are stored as template measurement data, wherein subsequent Doppler signal measurements and ECG signal measurements are compared with the template measurement data. Such template matching can be especially performed in such a way that, before using the device by the patient, a template measurement is done by medical staff, and, thus, subsequent patient measurements can be compared to this template in order to detect changes. When using such template matching, according to another preferred embodiment of the invention, for comparison with subsequent Doppler signal measurements and ECG signal measurements, the template data is corrected for the actual heart rate using the actual ECG signal and preferably for different postures of the patient based on the activity sensor of the respective subsequent measurement. Thus, the template can be corrected for different heart rates.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
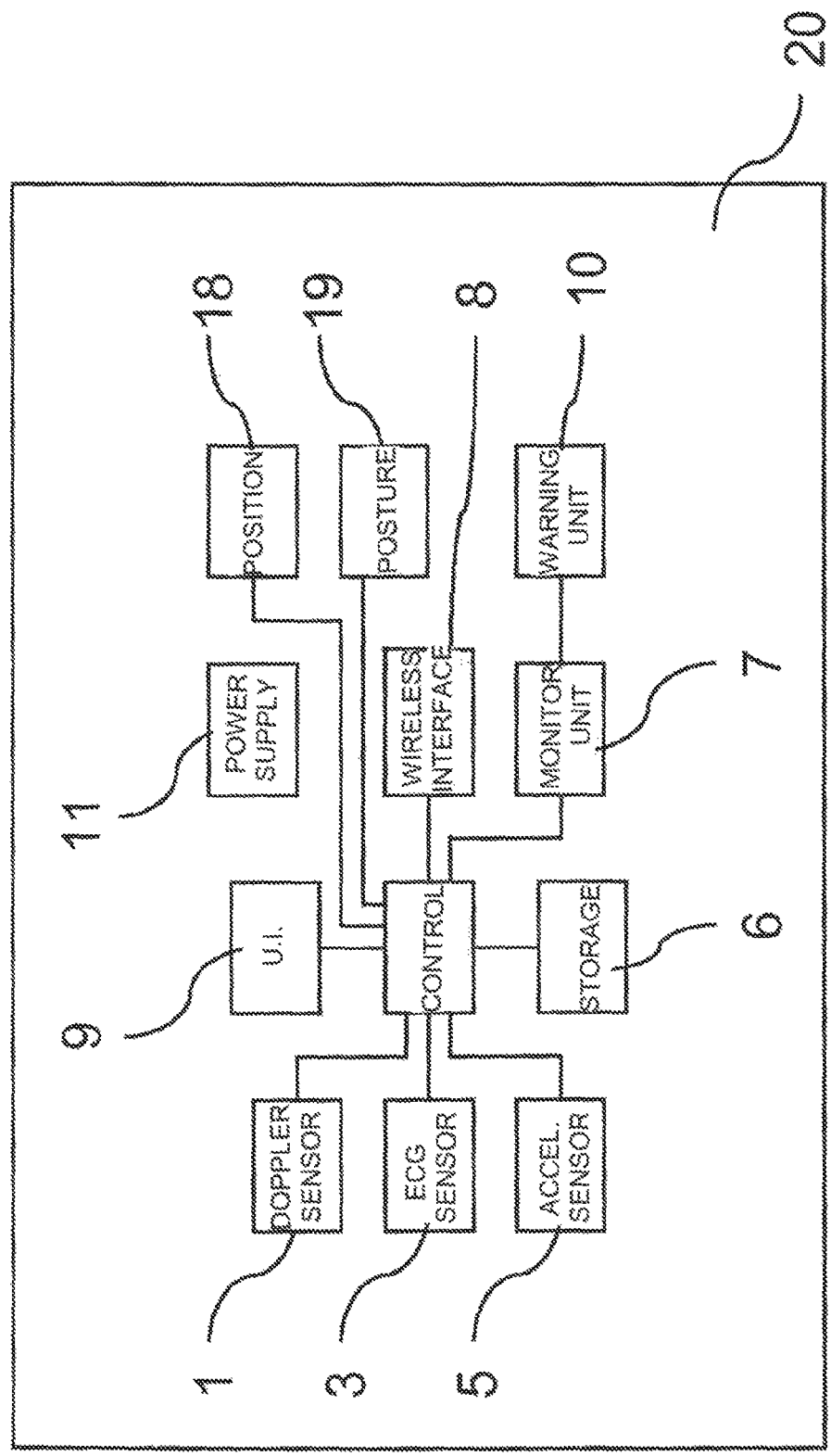
FIG. 1 is a block data diagram of the setup of a device for detection of electrical and mechanical cardio-vascular activities of a patient according to a preferred embodiment of the invention.

As can schematically be seen from FIG. 1, the device for detection of electrical and mechanical cardio-vascular activities of a patient according to a preferred embodiment of the invention comprises the following components:

A two-channel Doppler radar sensor 1 for detection of movements and movement direction with an incorporated transmitter for transmitting electromagnetic signals of a pre-defined frequency, e.g. 2.45 GHz, into the chest of the patient. For that, the Doppler radar sensor 1 comprises an oscillator operating in continuous mode. The Doppler radar sensor 1 further comprises a receiver for receiving the Doppler frequency shifted electromagnetic waves, which are reflected at boundary layers between areas of different electrical conductivities inside the body, in particular the heart wall. The Doppler radar signal received by Doppler radar sensor 1 is fed to a microcontroller 2.

Figure 2:
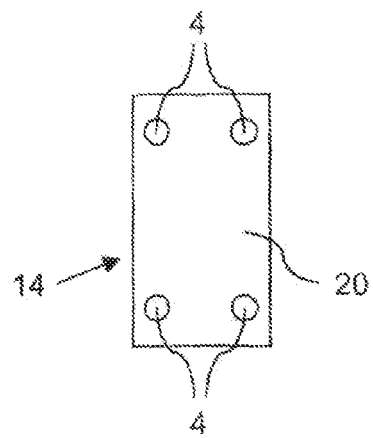
FIG. 2 is a top view on the device according to the preferred embodiment of the invention.

Further, an ECG unit 3 is provided, which is a 2-lead ECG front-end using dry metal electrodes 4, which can be better seen from FIG. 2. The ECG signal received by ECG unit 3 is also fed to microcontroller 2 which serves as common central control unit.

For posture and activity detection of the patient, an acceleration sensor 5 is provided which senses the patient's posture and movements in all spatial directions. Further, a storage 6 is provided for storing parameters of the Doppler radar signal and the ECG signal. Data stored in the storage 6 is monitored by a monitoring unit 7, analyzing the stored parameters, especially with respect to their trend. If analysis of the stored parameters indicates a critical health situation of the patient, a warning signal can be generated and output by warning unit 10.

The device according to the preferred embodiment of the invention further comprises a wireless interface 8 for wireless data communication with an external sender or receiver 12. This wireless interface 8 can be a Bluetooth or W-LAN interface for example. The device according to the preferred embodiment of the invention also comprises an user interface 9 which, dependant on the respective application may comprise buttons, displays etc.

The device further comprising a positioning indicator 18 for indicating a correct position of the device on the patient's chest and for indicating necessary movements of the device in order to achieve the correct position, based on the ECG signal. Additionally, a posture indicator 19 for indicating a correct posture of the patient and for indicating necessary movements of the patient in order to achieve the correct posture, based on the acceleration sensor signal is provided.

All these components are comprised in a casing 20 having a size of 10×3×5 cm$^3$, thus, allowing for a hand-held device 14, as also can be seen from FIG. 2. As shown in FIG. 1, a power supply 11, preferably as a rechargeable battery, is provided for supplying the electrical and electronical components of the device with electrical energy.

The physiological signals, i. e. the ECG signal and the Doppler radar signal, are sampled at 256 Hz, whereas the acceleration signal from the acceleration sensor 5 comprises a 25.6 Hz sampling frequency. Raw and processed data can be stored in the storage 6 of the device itself and/or transmitted via the wireless interface 8 to an external sender and receiver 12 which is shown in FIG. 3.

Figure 3:
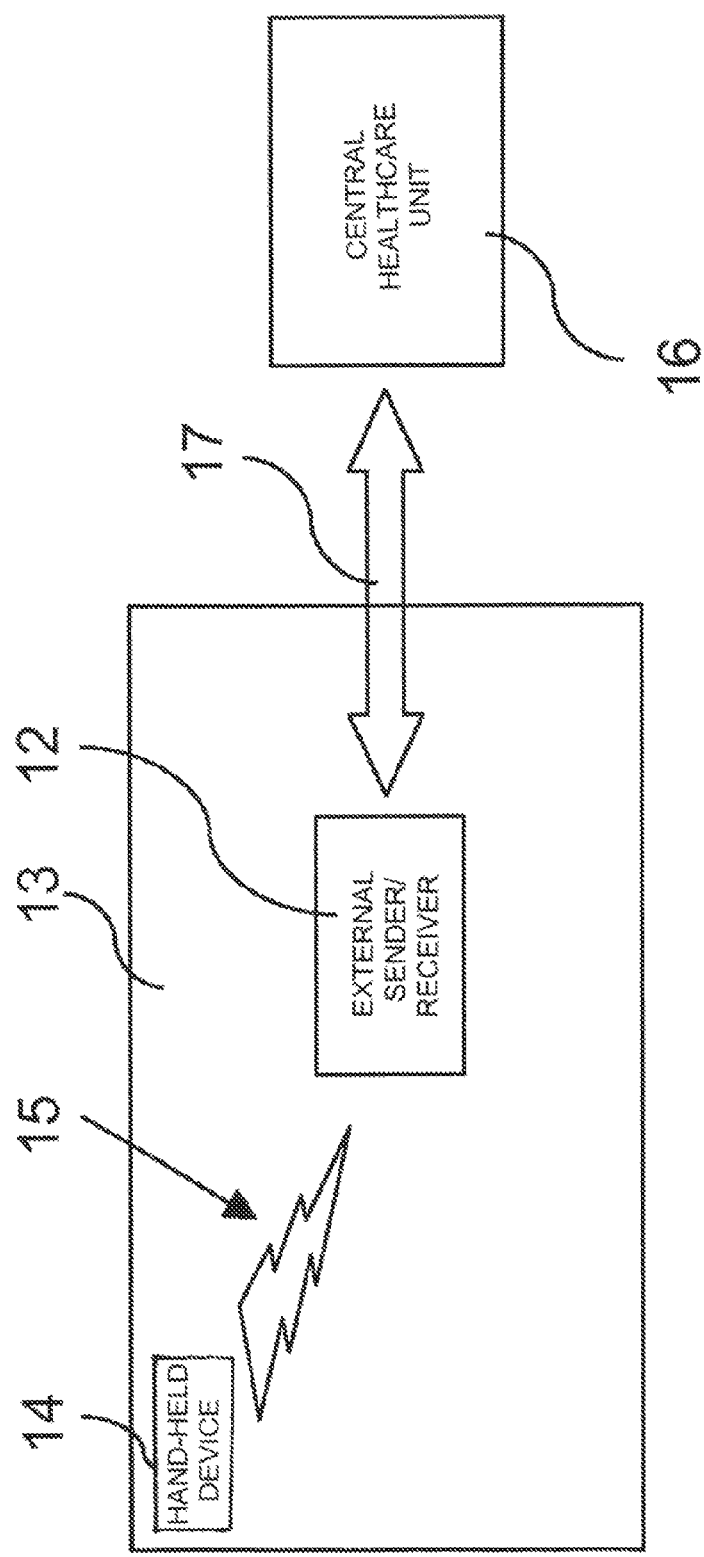
FIG. 3 is a block diagram of a system using the device according to the preferred embodiment of the invention.

FIG. 3 shows a block diagram of a system using the device according to the preferred embodiment of the invention a patient's home 13. As can be seen from FIG. 3, in the patient's home 13, data can be transmitted from the hand-held device 14 to the sender and receiver 12 and vice versa via a wireless connection 15. The sender and receiver 12 is connected to a central healthcare unit by a connection 17, e. g. via DSL or wirelessly via GSM, whereby the central healthcare unit 16 might be situated in a hospital where a healthcare professional has access to the received data. A typical measurement procedure with this system is given by the following sequence of stages:

1. The system triggers the patient to do measurements according to a schedule which is predefined by a healthcare professional. Such triggering can be done via visible and/or acoustical signals. The measurement intervals are stored in the storage 6 of the hand-held device 14 by the healthcare professional beforehand.
2. The patient performs the measurements and, thus, simultaneously measures ECG and Doppler radar signals, related to electrical and organ movement signals, respectively.
3. After each measurement, noise analysis is performed, and a new measurement is triggered if data quality is poor.
4. If the signal quality is sufficient, extraction of decompensation related measures like pre-ejection period, left ventricular ejection time etc. is performed.
5. The extracted parameters are stored in storage 6 of the hand-held device 14.
6. Analysis of the trend of the extracted parameters with signal processing techniques is performed in order to detect the onset of a decompensation phase.
7. If the onset of a decompensation is detected, the patient will be informed via the warning unit 10. The responsible healthcare professional will be informed via the central healthcare unit 16 which is connected to the sender and receiver 12 via DSL or GSM connection 17.

Figure 4:
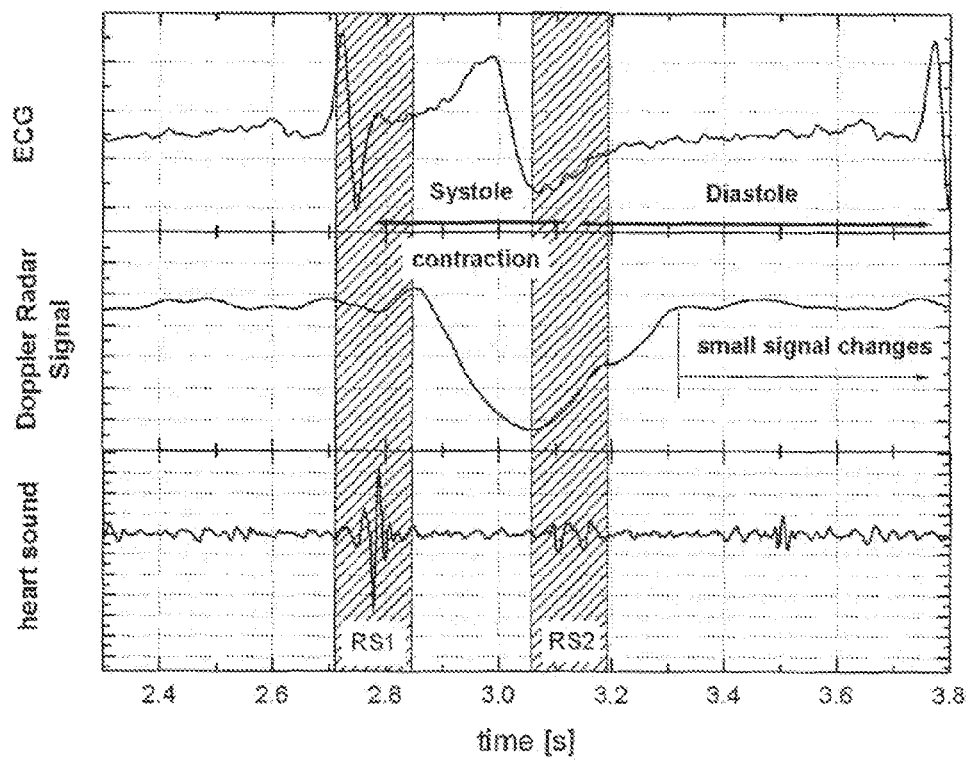
FIG. 4 is a graph showing the relations of an ECG signal, a Doppler radar signal, and a phonocardiogram.

From FIG. 4, an ECG signal and a Doppler radar signal captured simultaneously with the hand-held device 14, and, for comparison, a phonocardiogram captured with another device can be seen. For this graph, the Doppler radar signals where de-trended and low-pass filtered using a $4^{th}$ order Butterworth filter with a cut-off frequency of 20 Hz. The time intervals according to the heart sounds RS1 and RS2 are marked referencing the mechanical heart motion phases. Furthermore, it is visible that there is very little variation in the Doppler radar signal from approximately 520 ms after the R-peak until the next R-peak. This suggests that the resting phase of the heart during diastole can be identified using the radar Doppler sensor as well. Obviously, it is easily possible to detect the mechanically defined systole and diastole phase during a heart phase. Especially, the onset of the heart muscle contraction can be easily identified.

Heart performance parameters like pre-ejection period and left ventricular ejection time can be easily derived from these measured signals. These parameters and the analysis of their trend are good indicators for onset of a decompensation phase as well as they provide insights about the progression of decompensation.

As a result, a hand-held device is provided, that allows for simultaneous information on electrical and mechanical parameters of cardio-vascular activities related to well-defined heart motion phases. Even untrained patients can easily use this device, since a measurement does not need any special preparation in contrast to methods like bio-impedance and ultrasound. The device can be better repowered and, thus, can run for a couple of days when used for spot measurements only.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

Some features of the methods and devices described herein have already been described in the publication "A hand-held device for simultaneous detection of electrical and mechanical cardio-vascular activities with synchronized ECG and CW-Doppler radar" (J. Muehlsteff, J. Thijs, R. Pinter, G. Morren, G. Moesch), submitted to 29th IEEE EMBS Annul International Conference, received Apr. 2, 2007.

The invention claimed is:

1. A handheld device for configured to detect electrical and mechanical cardio-vascular activities of a patient, comprising:
   a case;
   a plurality of ECG electrodes mounted to the case and configured to contact the patient;
   a transmitter mounted in the case and configured to transmit electromagnetic signals of a predefined frequency into the patient,
   a receiver mounted in the case and configured to receive reflected Doppler frequency shifted electromagnetic waves to generate Doppler signal measurements;
   an ECG unit mounted in the case in electrical connection with the ECG electrodes and configured to capture an ECG signal of the patient's heart to generate ECG signal measurements;
   an acceleration sensor mounted in the case and configured to at least one of generate an acceleration sensor signal indicative of posture and activity of the patient; and
   a monitoring unit configured to detect cardiac decompensation of congestive heart failure by comparing the Doppler and ECG signal measurements with a template which is adjusted in accordance with the acceleration sensor signal and a heart rate derived from the ECG signal measurements.

2. The device according to claim 1, further comprising a wireless interface for wireless data communication with an external sender and/or receiver.

3. The device according to claim 1, further comprising a positioning indicator configured to indicate a selected position of the device on the patient's chest and/or to indicate movements of the device in order to position the device in the selected position, based on the ECG signal measurements and/or on the acceleration sensor signal.

4. The device according to claim 1, further comprising a posture indicator configured to indicate a posture of the patient based on the ECG signal measurements and on the acceleration sensor signal.

5. A device configured to detect electrical and mechanical cardio-vascular activities of a patient, comprising:
    a two-channel Doppler radar sensor including a transmitter and receiver which generate Doppler radar signals;
    an ECG unit which generates ECG signals;
    a microcontroller connected with the two-channel Doppler radar sensor and the ECG unit to receive the Doppler radar signals and the ECG signals;
    a storage which successively stores parameters of the Doppler radar signals and the ECG signals;
    a monitoring unit which analyzes the stored parameters for cardiac decompensation detection of congestive heart failure;
    a warning unit which generates a warning signal in response to the analysis of the stored parameters indicating a critical cardiac health situation of the patient; and
    a case which encloses the two-channel Doppler radar sensor, the ECG unit, the microcontroller, the storage, the monitoring unit and the warning unit and which supports one or more ECG electrodes, the case being configured to be held against the patient's chest with the one or more ECG electrodes in electrical contact with the chest.

6. The device according to claim 5, wherein the monitoring unit is configured to determine a trend from the stored parameters.

7. The device according to claim 5, wherein the monitoring unit is configured to:
    generate template data from the stored parameters of a first of the Doppler radar signals and a first of the ECG signals;
    comparing parameters of subsequent Doppler radar signals and ECG signals to the template data.

8. The device according to claim 7, further including:
    during the comparing, correcting for at least one of a patient activity, patient posture, and a heart rate of the patient.

9. A method for cardiac decompensation detection, comprising:
    from a case which is configured to be positioned against a patient's chest, transmitting electromagnetic signals of a predefined frequency into the chest of the patient;
    with a Doppler radar sensor in the case, detecting Doppler radar signals reflected in the patient's chest;
    with ECG electrodes on or in the case, detecting ECG signals of the patient's heart;
    storing at least one parameter of an initial Doppler signal measurement and of an initial ECG signal measurement as template measurement data;
    comparing subsequent Doppler signal measurements and subsequent ECG signal measurements with the template measurement data;
    deriving a heart rate from the ECG signal measurements;
    while comparing the subsequent Doppler signal measurements and the subsequent ECG signal measurements with the template data, correcting with the heart rate derived from the subsequent ECG signal measurements.

10. The method according to claim 9, further including:
    while comparing the subsequent Doppler signal measurements and the subsequent ECG signal measurements with the template data, correcting for at least one of posture and activity level of the patient derived from signals from an activity sensor.

11. The method according to claim 9, wherein the Doppler radar signals and the ECG signals are detected simultaneously.

12. The method according to claim 11, further including:
    storing parameters of the subsequent Doppler radar signal measurements and the subsequent ECG signal measurements;
    analyzing the stored parameters to determine a trend; and
    analyzing the trend of the stored parameters for an indication of a critical health situation of the patient.

* * * * *